United States Patent [19]

Jelks

[11] Patent Number: 5,616,125
[45] Date of Patent: Apr. 1, 1997

[54] APPARATUS FOR SIMULTANEOUSLY PUMPING MILK FROM THE RIGHT AND LEFT BREAST OF A NURSING MOTHER

[76] Inventor: Casandra N. Jelks, 9969 Archdale, Detroit, Mich. 48227

[21] Appl. No.: 519,723

[22] Filed: Aug. 28, 1995

[51] Int. Cl.⁶ ..................................................... A61M 1/06
[52] U.S. Cl. ............................................... 604/74; 601/14
[58] Field of Search ........................... 601/6, 14; 609/74, 609/75, 76

[56] References Cited

U.S. PATENT DOCUMENTS 5,514,166  5/1996  Silver et al. ............................... 604/74

Primary Examiner—Corrine M. McDermott
Assistant Examiner—N. Kent Gring

[57] ABSTRACT

An apparatus for simultaneously pumping milk from the right and left breast of a nursing mother comprising a nipple shield formed in a generally conical configuration with an exterior surface and an interior surface positionable over the nipple of a breast of a nursing mother. The shield has a centrally located aperture with a cylindrical coupling extension projecting from the exterior surface of the shield around the aperture. Further included is a pump. The pump has an input and an output. A flexible tube is provided and has an input end coupled to the conical extension of the shield and an output end coupled to the input of the pump. A housing is formed of a container with a separable cover. The container receives the pump and the end of the tube adjacent to its output end. A baby bottle is included and has an open top and positioned within the housing adjacent to the pair of pumps. A lid is removably positioned on the open top of the baby bottle with a large hole and a small hole for air exhaust. A supplemental tube couples the output of the pump to the large hole. A switch within the container is for activating the pump. A power source within the container with lines supplies power to the pump through the switch. Straps coupled to the container are positionable about the shoulders of the user to releasably secure the container to the back of the user.

2 Claims, 3 Drawing Sheets

APPARATUS FOR SIMULTANEOUSLY PUMPING MILK FROM THE RIGHT AND LEFT BREAST OF A NURSING MOTHER

BACKGROUND OF THE INVENTION

1. Field of the Invention

The present invention relates to an apparatus for simultaneously pumping milk from the right and left breast of a nursing mother and, more particularly, pertains to supporting a breast milk pumping system on the back of a nursing mother.

2. Description of the Prior Art

The use of breast pumps of various designs and configurations is known in the prior art. More specifically, breast pumps of various designs and configurations heretofore devised and utilized for the purpose of pumping and storing the milk of nursing mothers by various methods and apparatuses are known to consist basically of familiar, expected, and obvious structural configurations, notwithstanding the myriad of designs encompassed by the crowded prior art which has been developed for the fulfillment of countless objectives and requirements.

By way of example, the prior art discloses in U.S. Pat. No. 4,772,262 to Grant discloses a portable electric breast pump including vacuum pump, vacuum hose, collection container and a milk pumping flange.

U.S. Pat. No. 4,892,517 to Yuan and Joss discloses an improved breast pump comprised of a manifold having a cavity and plurality of openings.

U.S. Pat. No. 4,961,726 to Richter discloses a breast milk pump suction arrangement including a suction pump with suction connections, a fellow breast connector, a reservoir connected to the funnel and a pulsator.

U.S. Pat. No. 5,009,638 to Riedwig et al. discloses a breast pump comprising of a milk reservoir and a flanged closure member for connection with the reservoir.

U.S. Pat. No. 5,295,957 to Aida et also discloses a breast pump having a pressure adjusting mechanism.

Lastly, U.S. Pat. No. Des. 251,015 to Cone discloses a breast pump.

In this respect, the apparatus for simultaneously pumping milk from the right and left breast of a nursing mother according to the present invention substantially departs from the conventional concepts and designs of the prior art, and in so doing provides an apparatus primarily developed for the purpose of supporting a breast milk pumping system on the back of a nursing mother.

Therefore, it can be appreciated that there exists a continuing need for a new and improved apparatus for simultaneously pumping milk from the right and left breast of a nursing mother which can be used for supporting a breast milk pumping system on the back of a nursing mother. In this regard, the present invention substantially fulfills this need.

SUMMARY OF THE INVENTION

In view of the foregoing disadvantages inherent in the known types of breast pumps of various designs and configurations now present in the prior art, the present invention provides an improved apparatus for simultaneously pumping milk from the right and left breast of a nursing mother. As such, the general purpose of the present invention, which will be described subsequently in greater detail, is to provide a new and improved apparatus for simultaneously pumping milk from the right and left breast of a nursing mother and method which has all the advantages of the prior art and none of the disadvantages.

To attain this, the present invention essentially comprises a new and improved apparatus for simultaneously pumping milk from the right and left breast of a nursing mother comprising, in combination, a pair of nipple shields including a left shield and a right shield. Each of the shields are formed in a generally conical configuration with an exterior surface and an interior surface positionable over the nipple of a breast of a nursing mother. Each of the shields has a centrally located aperture with a cylindrical coupling extension projecting from the exterior surface of the shield around the aperture. A pair of independently operable pumps include a left pump and a right pump. Each of the pumps has an input and an output. A pair of flexible tubes include a left tube and a right tube. The left tube has an input end coupled to the conical extension of the left shield and an output end coupled to the input of the left pump. The right tube has an input end coupled to the conical extension of the right shield and an output end coupled to the input of the right pump. A housing is formed of a container with a separable cover. The container receives the pair of pumps and the ends of the tubes adjacent to their output ends. A baby bottle is provided and has an open top and positioned within the housing adjacent to the pair of pumps. A lid is removably positioned on the open top of the baby bottle with two large holes and one small hole. The small hole is for air exhaust. A pair of supplemental tubes is provided. One supplemental tube couples the output of the left pump to one large hole and the other supplemental tube couples the output of the right pump to the other large hole. A pair of switches within the container include a left switch for activating the left pump to the exclusion of the right pump and a right switch for activating the right pump to the exclusion of the left pump. A power source within the container with lines in parallel supplies power to the two pumps through the two switches. Straps coupled to the container are positionable about the shoulders of the user to releasably secure the container to the back of the user.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved apparatus for simultaneously pumping milk from the right and left breast of a nursing mother which has all the advantages of the prior art breast pumps of various designs and configurations and none of the disadvantages.

It is another object of the present invention to provide a new and improved apparatus for simultaneously pumping milk from the right and left breast of a nursing mother which may be easily and efficiently manufactured and marketed.

It is a further object of the present invention to provide a new and improved apparatus for simultaneously pumping milk from the right and left breast of a nursing mother which is of a durable and reliable construction.

An even further object of the present invention is to provide a new and improved apparatus for simultaneously pumping milk from the right and left breast of a nursing mother which is susceptible of a low cost of manufacture with regard to both materials and labor, and which accordingly is then susceptible of low prices of sale to the consuming public, thereby making such breast pumps of various designs and configurations economically available to the buying public.

Still yet another object of the present invention is to provide a new and improved apparatus for simultaneously pumping milk from the right and left breast of a nursing mother which provides in the apparatuses and methods of the prior art some of the advantages thereof, while simultaneously overcoming some of the disadvantages normally associated therewith.

Even still another object of the present invention is to support a breast milk pumping system on the back of a nursing mother.

Lastly, it is an object of the present invention to provide an apparatus for simultaneously pumping milk from the right and left breast of a nursing mother comprising a nipple shield formed in a generally conical configuration with an exterior surface and an interior surface positionable over the nipple of a breast of a nursing mother. The shield has a centrally located aperture with a cylindrical coupling extension projecting from the exterior surface of the shield around the aperture. Further included is a pump. The pump has an input and an output. A flexible tube is provided and has an input end coupled to the conical extension of the shield and an output end coupled to the input of the pump. A housing is formed of a container with a separable cover. The container receives the pump and the end of the tube adjacent to its output end. A baby bottle is included and has an open top and positioned within the housing adjacent to the pair of pumps. A lid is removably positioned on the open top of the baby bottle with a large hole and a small hole for air exhaust. A supplemental tube couples the output of the pump to the large hole. A switch within the container is for activating the pump. A power source within the container with lines supplies power to the pump through the switch. Straps coupled to the container are positionable about the shoulders of the user to releasably secure the container to the back of the user.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
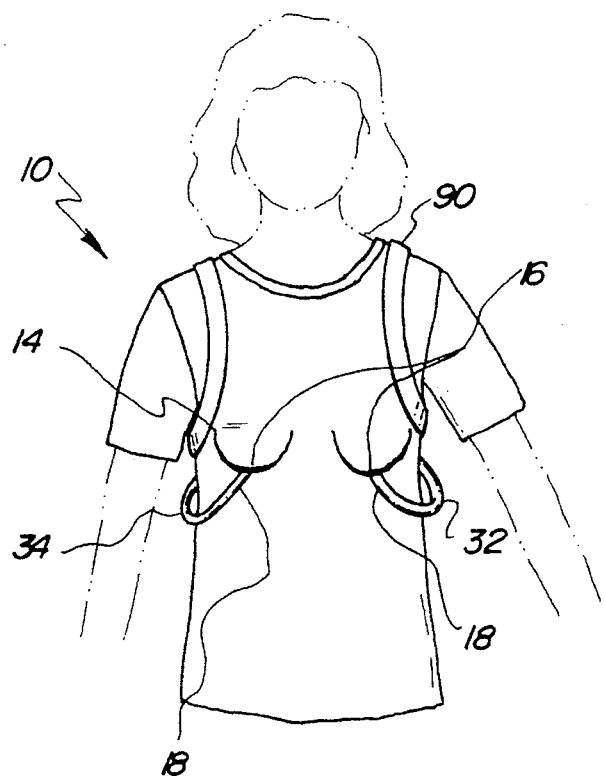
FIG. 1 is a perspective illustration of the preferred embodiment of the new and improved apparatus for simultaneously pumping milk from the right and left breast of a nursing mother constructed in accordance with the principles of the present invention.

With reference now to the drawings, and in particular to FIG. 1 thereof, the preferred embodiment of the new and improved apparatus for simultaneously pumping milk from the right and left breast of a nursing mother embodying the principles and concepts of the present invention and generally designated by the reference numeral 10 will be described.

The present invention, the new and improved apparatus for simultaneously pumping milk from the right and left breast of a nursing mother, is a system 10 comprised of a plurality of components. In their broadest context, the components include a nipple shield, a pump, a flexible tube, a housing, a baby bottle, a lid, a supplemental tube, a switch, a power source, and straps. Each of the individual components is specifically configured and correlated one with respect to the other so as to attain the desired objectives.

Figure 2:
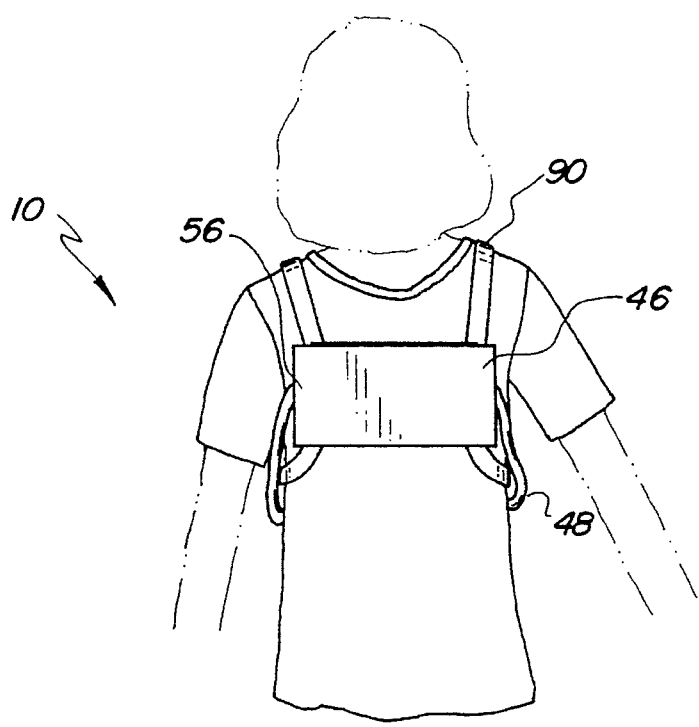
FIG. 2 is a rear perspective view of the apparatus shown in FIG. 1.
Figure 3:
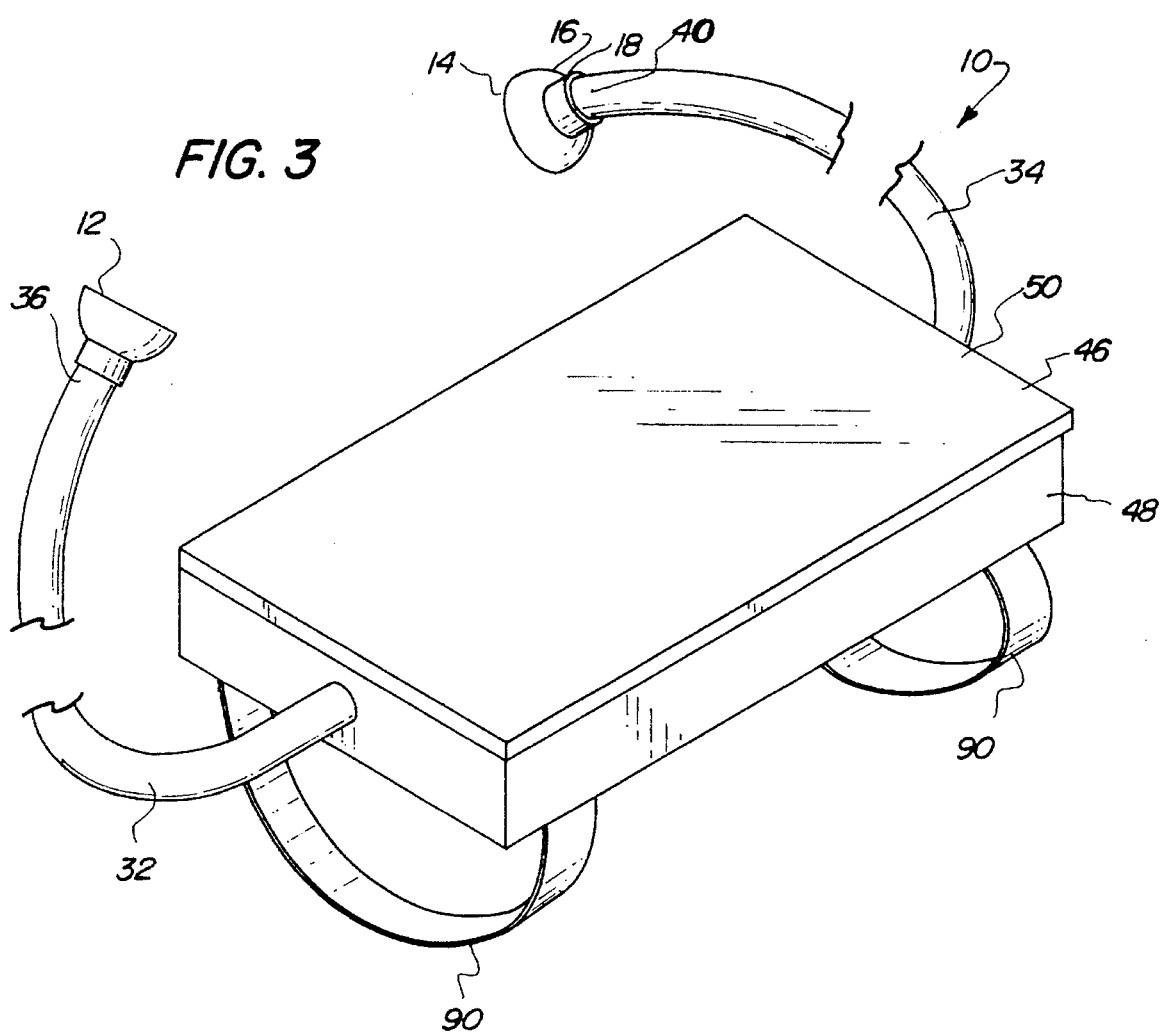
FIG. 3 is a perspective illustration of the apparatus of the prior Figure shown removed from the nursing mother.
Figure 4:
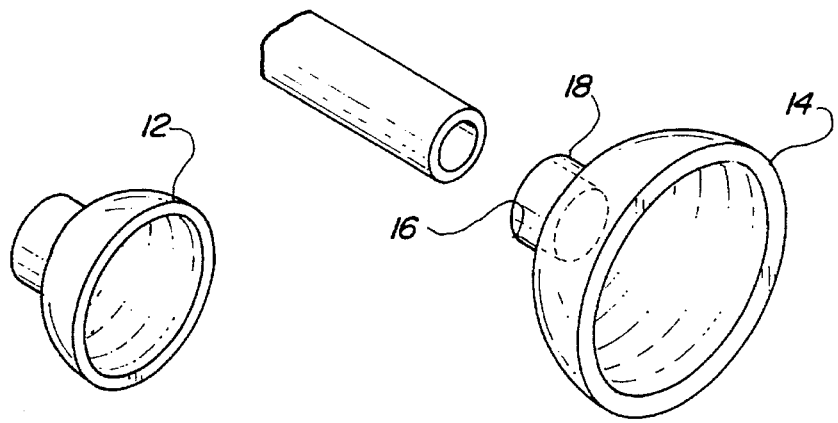
FIG. 4 is an enlarged perspective view of the shields and a portion of a hose.
Figure 5:
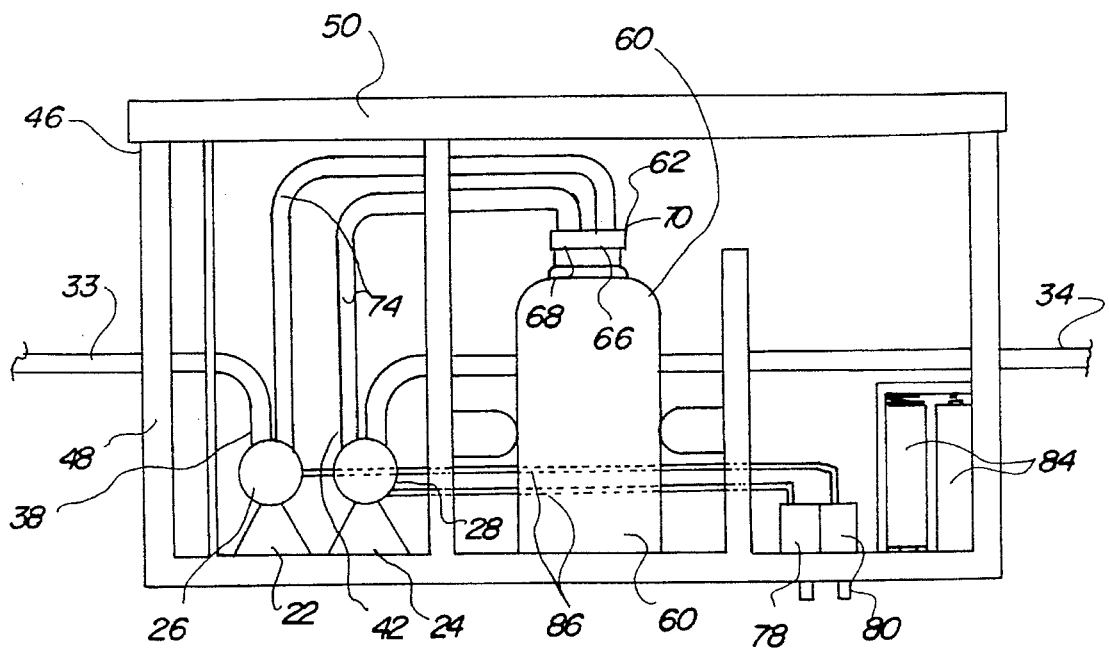
FIG. 5 is a side elevational view of the container of the prior Figures with one side removed to show the internal constructions thereof.

More specifically, the system 10 of the present invention is best seen in FIGS. 1, 2 and 3. It is a system designed for simultaneously pumping milk from the two breasts of a nursing mother. It should be understood, however, that it may be used to pump from one breast or the other at any one time to exclusion of the other breast.

Contact with the breast of the mother is made through a pair of nipple shields. The nipple shields include a left nipple shield 12 and a right nipple shield 14. Each of the shields is formed from a generally cone shaped configuration. It has an exterior surface and an interior surface. The interior surface is positionable over the breast of the nursing mother. Each of the shields is also formed to have a centrally located aperture 16. Associated with each aperture is a cylindrical coupling extension 18. Such extensions project rearwardly from the exterior surface of the shield from a location where they couple with the shield at a region around the aperture.

Next provided are a pair of independently operable pumps. Such pumps include a left pump 22 and a right pump 24. Each of the pumps has an input 26 and an output 28.

Operably located between the left shield and the left pump and the right shield and the right pump respectively are a pair of flexible tubes. Such tubes include a left tube 32 and a right tube 34. The left tube has an input end 36 coupled to the conical extension of the left shield. The left tube also has an output end 38 coupled to the input of the left pump. The right tube also has an input end of 40 coupled to the conical extension of the right shield. It also has an output end 42 coupled to the input of the right pump.

Operable in association with the output ends of the tubes as well as the pumps is a housing 46. The housing is formed of a container 48 with a separable cover 50. The container receives the pair of pumps 22, 24 and the ends 56 of the tubes adjacent to their output ends.

Also located within the container is a baby bottle 60. The baby bottle is readily removable from the container. The bottle has an open top 62. It is positioned within the housing adjacent to the pair of pumps.

Removably positioned on the open top of the baby bottle is a lid 66. The lid is provided with two large holes 68 and one small hole 70. The small hole is for air exhaust. The large holes are for receiving the milk pumped from the nursing mother. A pair of supplemental tubes 74 are next provided. One of the supplemental tubes couples the output of the left pump to one large hole. The other supplemental tube couples the output of the right pump to the other large hole.

In association with the pumps and also located within the container, are a pair of switches within the container. Such switches include a left switch 78 for activating the left pump to the exclusion of the right pump. A right switch 80 is for activating the right pump to the exclusion of the left pump. The switches are located on the exterior surface of the container and may be independently utilized to activate or inactivate its individual associated pump.

Lastly provided within the container is a power source 84. Such power source is shown as a pair of batteries. In association therewith electrical lines 86 are provided in parallel for supplying power to the two pumps through the two switches.

Lastly provided are a pair of straps 90. The straps are coupled to the container. There positionable about the shoulders of the nursing mother to releasably secure the container to the back of the nursing mother. Compare FIGS. 1 and 2.

Figure 6:
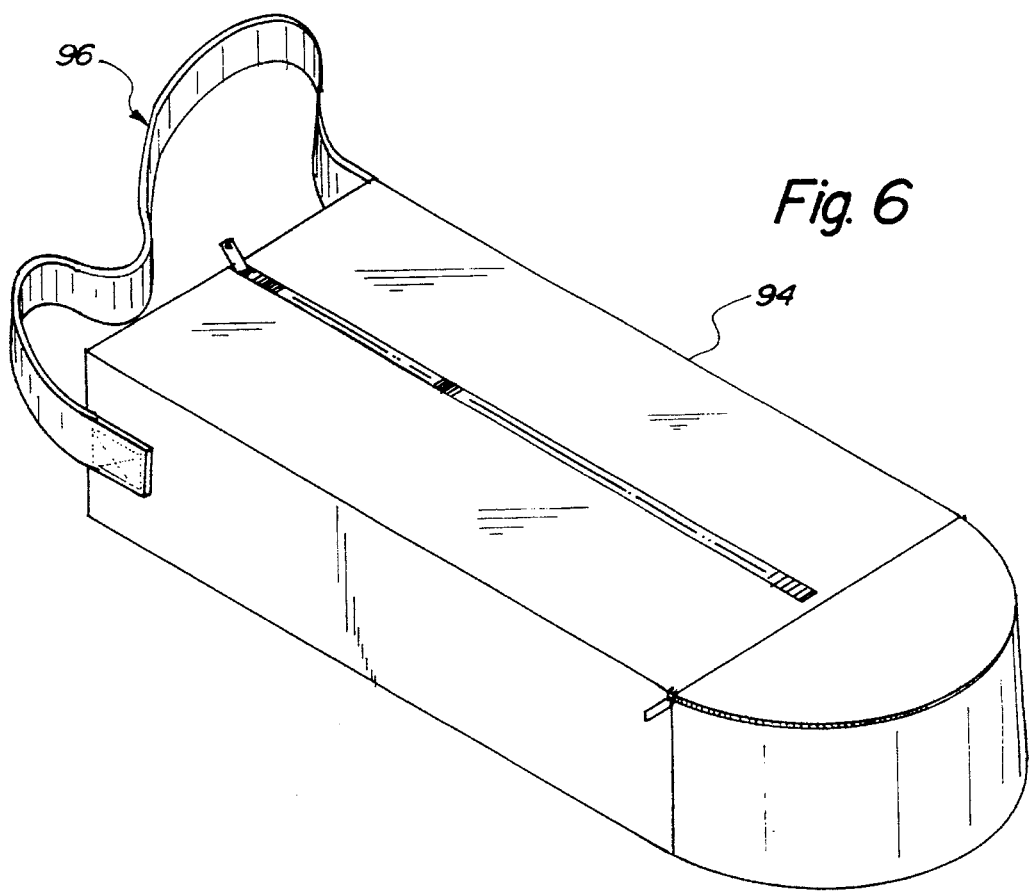
FIG. 6 is a perspective view of a case for supporting the apparatus of the prior Figure.

FIG. 6 shows an optional feature of the invention. Such optional feature is a storage case 94 in a generally rectangular configuration with a sliding fastener for opening the storage case for the receipt and storage of the system of the present invention. A carrying strap 96 is provided for convenience in the transporting of the storage case and its stored contents.

The concept of the present invention is a battery-operated breast pump that can be strapped on to automatically pump breast milk while leaving the mother's hands free to do other things.

The form of the present invention consists of a carrying case with compartments for a pump and a milk bottle. The pump compartment contains the pump, battery pack, milk container, a set of attached shoulder straps, and two plastic tubes with suction cups. A cotton t-shirt designed for nursing also accompanies the device.

The function of the present invention is achieved by a simple process. Put on the nursing t-shirt. Open the carrying case and take out the pump. Slip on the shoulder straps so the milk container is positioned on the back between the shoulder blades and under the shirt. Place a suction cup on each breast. Turn on the pump to suction milk from both breasts. The milk flows through the tubing to the milk container. When finished, take off the cups, slide off the straps, rinse the device, and store it in the case. Refrigerate the milk in a bottle or other container.

The present invention has numerous attributes. The present invention is a time-saving device for nursing mothers. Its strap-on design leaves their hands free for tending to children or doing other things. The dual suction cups pump both breasts at once, unlike other pumps that come with only one and take twice as long to perform the same function. No precious milk is wasted because mothers can pump on a regular schedule. Babies will still get the benefits of breast milk, and mothers can store the milk for bottles for feedings when they cannot be home.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved apparatus for simultaneously pumping milk from the right and left breast of a nursing mother comprising, in combination:

a pair of nipple shields including a left shield and a right shield, each of the shields formed in a generally conical configuration with an exterior surface and an interior surface positionable over the nipple of a breast of a nursing mother, each of the shields having a centrally located aperture with a cylindrical coupling extension projecting from the exterior surface of the shield around the aperture;

a pair of independently operable pumps including a left pump and a right pump, each of the pumps having an input and an output;

a pair of flexible tubes including a left tube and a right tube, the left tube having an input end coupled to the conical extension of the left shield and an output end coupled to the input of the left pump, the right tube having an input end coupled to the conical extension of the right shield and an output end coupled to the input of the right pump;

a housing formed of a container with a separable cover, the container receiving the pair of pumps and the ends of the tubes adjacent to their output ends;

a baby bottle having an open top and positioned within the housing adjacent to the pair of pumps;

a lid removably positioned on the open top of the baby bottle with two large holes and one small hole, the small hole being for air exhaust;

a pair of supplemental tubes, one supplemental tube coupling the output of the left pump to one large hole and the other supplemental tube coupling the output of the right pump to the other large hole;

a pair of switches within the container including a left switch for activating the left pump to the exclusion of the right pump and a right switch for activating the right pump to the exclusion of the left pump;

a power source within the container with lines in parallel supplying power to the two pumps through the two switches; and straps coupled to the container positionable about the shoulders of the user to releasably secure the container to the back of the user.

2. An apparatus for simultaneously pumping milk from the right and left breast of a nursing mother comprising:

a pair of nipple shields each formed in a generally conical configuration with an exterior surface and an interior surface positionable over the nipple of a breast of a nursing mother, each shield having a centrally located aperture with a cylindrical coupling extension projecting from the exterior surface of the shield around the aperture;

a pair of pumps each having an input and an output;

a pair of flexible tubes each having an input end coupled to the conical extension of an associated shield and an output end coupled to the input of an associated pump;

a housing formed of a container with a separable cover, the container receiving the pair of pumps and the ends of the tubes adjacent to their output ends;

a baby bottle having an open top and positioned within the housing adjacent to the pair of pumps;

a lid removably positioned on the open top of the baby bottle with two large holes and a small hole for air exhaust;

a pair of supplemental tubes coupling the outputs of the pumps to the large holes;

a pair of switches within the container for activating the pumps; and a power source within the container with lines supplying power to the pump through the switches.

* * * * *